United States Patent [19]
Bortz et al.

[11] Patent Number: 6,040,914
[45] Date of Patent: Mar. 21, 2000

[54] SIMPLE, LOW COST, LASER ABSORPTION SENSOR SYSTEM

[75] Inventors: Michael L. Bortz, Palo Alto; Asif A. Godil, Mountain View, both of Calif.

[73] Assignee: New Focus, Inc., Santa Clara, Calif.

[21] Appl. No.: 08/872,617

[22] Filed: Jun. 10, 1997

[51] Int. Cl.⁷ .......................... G01N 21/31; G01N 21/39
[52] U.S. Cl. ........................................... 356/435; 250/345
[58] Field of Search .................................... 356/435, 437, 356/438, 439; 250/343, 345

[56] References Cited

U.S. PATENT DOCUMENTS

| | | |
|---|---|---|
| 4,297,035 | 10/1981 | Bjorklund . |
| 4,523,847 | 6/1985 | Bjorklund et al. . |
| 4,594,511 | 6/1986 | Cooper et al. . |
| 4,849,637 | 7/1989 | Cerff et al. . |
| 4,934,816 | 6/1990 | Silver et al. . |
| 5,015,099 | 5/1991 | Nagai et al. ............................. 356/437 |
| 5,134,279 | 7/1992 | Hobbs ..................................... 250/345 |
| 5,301,014 | 4/1994 | Koch ...................................... 356/437 |
| 5,317,156 | 5/1994 | Cooper et al. . |
| 5,319,668 | 6/1994 | Lueke . |
| 5,528,040 | 6/1996 | Lehmann ................................ 356/439 |
| 5,530,541 | 6/1996 | Ahn et al. . |

OTHER PUBLICATIONS

Michael Bortz and Tim Day, "Diode Lasers Monitor Vapor Deposition", Laser Focus World, Nov. 1996.

Kurt L. Haller and Philip C.D. Hobbs "Double Beam Laser Absorption Spectroscopy: Shot Noise–Limited Performance at Baseband With A Novel Electronic Noise Canceller", SPIE vol. 1435 Optical Methods for Ultrasensitive Detection and Analysis: Techniques and Applications (1991).

D.T. Cassidy and J. Reid "Atmospheric Pressure Monitoring Of Trace Gases Using Tunable Diode Laser", Applied Optics, vol. 21, No. 7, Apr. 1, 1982.

Mark G. Allen et al., "Ultrasensitive Diode Laser Direct Absorption Measurements: Applications To Mass Flux Flight Instrumentation", SPIE vol. 2122, pp. 2–12.

*Primary Examiner*—Richard A. Rosenberger
*Attorney, Agent, or Firm*—Beyer & Weaver, LLP

[57] ABSTRACT

A laser absorption sensor system for performing optical measurements on a sample is described. The sensor system includes a tunable laser, capable of being tuned at rates exceeding 1 KHZ, and with a tuning range approaching 1 GHz. The laser beam is modulated at a modulation frequency between 1 and 100 KHz. Modulation in this frequency range is termed wavelength modulation. The beam is split into two beams, a signal beam and a reference beam. The signal beam traverses the sample where characteristic absorption takes place and is incident on a signal photodetector. The reference beam is incident directly on a reference photodetector. A noise cancellation circuit combines signal and reference photo-currents from signal and reference photodetectors reducing signal noise and increasing system sensitivity. The combination of wavelength modulation and the noise cancellation scheme provide a highly sensitive simple, rugged, low cost laser absorption sensor system.

5 Claims, 7 Drawing Sheets

SIMPLE, LOW COST, LASER ABSORPTION SENSOR SYSTEM

BACKGROUND OF THE INVENTION

The field of the invention relates to laser based sensing systems. In particular, the field of the invention relates to a laser based optical absorption system characterized by high sensitivity, high stability, ease of use and low cost.

Sensing devices using optical absorption to measure characteristics of a sample species are well known. These devices generally use a laser to generate light that is passed through a sample gas or vapor where characteristic absorption occurs altering the intensity of the beam. A photodetector measures the intensity of the altered beam. By tuning the laser over a range of frequencies one can determine various characteristics of atoms or molecules within the species such as chemical composition, concentration, propagation direction, and velocity distribution.

A principal advantage of using optical absorption for determining such characteristics of a sample is that it is non-invasive; the devices generating and receiving the laser light do not have to be located in or necessarily near the species being measured. This can be crucial if the species, for example, is of a toxic nature or if contamination of the system is to be avoided.

In addition, optical sensing systems based on lasers are highly sensitive and selective. Such devices can accurately measure trace amounts of atomic or molecular species in a sample gas or vapor without interference of other species within the sample. This is useful for a variety of applications, including toxic gas detection, trace element detection and combustion diagnostics. In other applications such as thin film process control, detection of the velocity of species is also important, since both the velocity and concentration of a species determine the rate at which the species is deposited on a surface.

In general, these applications require detection of the species of interest with the highest sensitivity possible. The sensitivity of the system is determined by the signal to noise ratio (SNR), or the ratio of the laser absorption signal to the signal due to noise in the system. The highest sensitivity is obtained by maximizing the absorption signal from the gas while minimizing the signal due to noise in the system. For most applications the signal strength is fixed by the properties of the sample so that to increase sensitivity one must reduce the noise.

Various conventional schemes have been previously employed to reduce noise in laser absorption systems. The primary source of noise in such systems is the laser. A typical diode laser has a noise spectrum that increases rapidly at low detection frequencies. Thus, low frequency detection schemes are inherently more noisy (less sensitive) than high frequency detection schemes. This fact is well known and has led to the use of frequency modulation (FM) detection schemes (see U.S. Pat. No. 5,530,541). In FM detection the laser beam is passed through a frequency modulator which periodically shifts the laser beam frequency at a predetermined modulation frequency. The beam is then passed through the sample where the characteristic absorption takes place. The modified beam is then directed onto a detector which outputs an electrical current proportional to the intensity of the incident beam. The desired absorption information is contained in the component of the detector signal at the modulation frequency and can be extracted using a phase sensitive lock-in amplifier.

By upshifting the detection frequency from DC, where the laser noise is high to the modulation frequency, such methods greatly increase sensitivity. However, modulation frequencies typically greater than 50 MHz must be used in order to shift the detection frequency to a range where laser noise becomes negligible. Modulation frequencies of this magnitude require radio frequency (RF) electronics (oscillators, amplifiers, splitters and mixers) for signal processing. These components are complicated, expensive and susceptible to drift and other problems. In addition, the photodetector size used must be reduced linearly as the modulation frequency is increased. Modulation frequencies greater than 50 MHz require very small detectors which complicate alignment of the laser beam.

Other conventional schemes for increasing sensitivity for a laser absorption system include the method of Hobbs, U.S. Pat. No. 5,134,276. Hobbs attempts to reduce laser noise by using a noise cancellation scheme in which the laser beam is divided into a reference and a signal beam. The reference beam is directed to a reference photodetector and the signal beam is passed through the sample, where characteristic absorption takes place and is then directed to a signal photodetector. The photodetector outputs a photocurrent proportional to the intensity of incident light on the detector's surface. The reference photo-current is scaled such as to match its DC component to the DC component of the signal photo-current. The scaling is done such that substantially all components of the reference photo-current are scaled proportionally. The reference photo-current is then subtracted from the signal photo-current to produce a so-called autobalanced photo-current. The autobalanced photo-current eliminates any noise common to both reference and signal photo-currents, but retains the absorption signal down to low frequencies since it is contained in the signal photo-current alone.

This procedure reduces laser noise, however, it cannot cancel any noise that is not common to both the signal and reference beams. Shot noise is one type of such uncorrelated noise. Shot noise is a random current fluctuation that occurs when light is detected. Standard photodetectors pass current from their anode to their cathode in proportion to the number of photons incident on the detector surface. One electron is passed for each photon detected. The detection of photons, as governed by quantum mechanics, is a probalistic process. The current of the photodetector thus will be subject to random fluctuations, the size of which are determined by the standard deviation of the photon detection probability distribution. These fluctuations will be completely uncorrelated between the two photodetectors and thus cannot be canceled. In addition, any other sources of uncorrelated noise will not be canceled by the method of Hobbs. In particular any noise introduced to either beam after the laser beam is split will not be canceled.

Furthermore, conventional implementations of the Hobbs circuit in laser absorption sensing systems, as in *Double beam laser absorption spectroscopy: shot noise-limited performance at baseband with a novel electronic noise canceler*, Kurt L. Haller and Philip C. D. Hobbs, SPIE Vol 1435 Optical Methods for Ultrasensitive Detection and Analysis: Techniques and Applications (1991), use a diode laser without an integral grating for tuning, and direct detection (no modulation imparted on the laser beam) with the final output being derived from the log output of the Hobbs circuit. Such systems have many deficiencies, including: (a) poor spectral control, i.e. the laser wavelength is sensitive to temperature, optical feedback and other environmental effects, (b) there is no simple tuning mechanism for the laser, (c) the output is intrinsically temperature sensitive, (d) the output has a nonzero baseline, so that when the absorption is zero the absorption signal is not zero, (e) the baseline signal depends on the split ratio of the signal and reference beams, (f) scanning away from the absorption line is necessary for calibration because of the non-zero baseline signal, (g) the detection technique occurs essentially at DC, thus the system is sensitive to low frequency and acoustic noise; any low frequency noise inherent in the electronics or otherwise occurring after the splitting of the signal and reference beams will not be canceled and will reduce the sensitivity of such a conventional system, and (h) variations in the optical transmission of the signal path can only be corrected by scanning the absorption line.

Therefore, what is needed is a laser absorption system that is characterized by high sensitivity; preferably such a system should have the capability of sensing very small absorptions at the theoretical limit.

What is also needed is a laser absorption sensor system characterized by a large dynamic range, such that it has the capability to sense both small and large absorptions with no modification.

What is also needed is a laser absorption system characterized by high accuracy. Such a system would be very valuable for certain applications in which the detection and extraction of the velocity of the species are important. For example, in thin film process control measurement of the species concentration and species velocity provides species flux. The flux determines the deposition or growth rate of a film on a surface. The ability to determine flux with greater accuracy would enable a thin film to be deposited over geometrically complex surfaces with greater precision than is possible using conventional laser absorption techniques.

What is also needed is a laser absorption system characterized by low drift. That is, the output of the sensor should be time invariant when the absorption being measured is time invariant.

What is also needed is a laser absorption system with zero baseline output signal, so that when the absorption is zero, the output signal is also zero.

Additionally, what is needed is a laser absorption system with an output that is substantially independent of temperature. What is also needed is a laser absorption system with an output that is substantially independent of transmission variations through the sample region that are unrelated to absorption in the species of interest; this could occur if additional, or partially opaque, windows were placed in the beam path. Such a system would be very valuable for accurately determining the concentration of a specific species within a gas sample.

Finally, it would be desirable to achieve the foregoing objectives for a sensor system in a practical commercially viable manner. That is, the laser absorption system should be manufacturable with as few components as possible to reduce cost. Such a system ideally should have subcomponents which comprise commercially available low cost, low frequency electronics rather than high frequency specialized circuitry. In addition, such a system ideally should be rugged and capable of being operated by a user without the need for continual adjustment or recalibration.

SUMMARY OF THE INVENTION

An aspect of the invention is directed to an apparatus that satisfies the need for a highly sensitive, simple, rugged, low cost laser absorption sensing system. The apparatus comprises a tunable diode laser employing a diffraction grating element to obtain high wavelength selectability, a signal source, a beam splitter, a sample region, a two channel optical detector and demodulating and autobalancing circuitry. In an aspect of the invention a tunable diode laser is modulated at a frequency between 1 and 100 KHz. By choosing a modulation frequency above 1 KHz, noise due to background optical radiation reaching the detectors or electrical noise from simple preamplifier circuits is avoided. In addition, modulation frequencies of less than 100 KHz allow for the use of simple, low cost, and stable signal processing electronics. Modulation in this frequency range is called wavelength modulation (WM). A two channel photodetector and an autobalancing circuit such as that of Hobbs are used to cancel laser noise and obtain substantially shot noise limited performance.

A signal between 1 and 100 KHz (the modulation frequency) is generated by the signal source and used to periodically tune the laser frequency. This can be accomplished by mechanical motion of the laser grating or mirror or by electrical means such as current modulation. The modulated laser beam is then passed through a beam splitter which passes approximately half of the beam intensity and reflects the other portion creating two beams, a signal and a reference beam. The reference beam is directed to one channel of the photodetector. The signal beam is passed through the sample region where a portion of it is absorbed by the sample. The altered signal beam is then directed to the other channel of the two channel detector. Each channel of the photodetector outputs a photocurrent proportional to the intensity of light incident on the detector surface of that channel. Thus a signal and a reference photo-current are generated by the detector. The signal and reference photo-currents are processed by the autobalancing circuitry, which matches their respective DC components and then subtracts the reference photo-current from the signal photo-current, outputting the so-called autobalanced signal. The autobalanced signal contains the desired absorption information of the sample along with any noise from the signal and reference photo-currents that is uncorrelated. This amounts essentially to the shot noise of the detector. The autobalanced photo-current is then demodulated, extracting a DC signal proportional to the magnitude of the modulation frequency component of the autobalanced signal. This signal is normalized by dividing it by the DC component of the signal photo-current thus creating an output that is independent of the total laser intensity.

In an embodiment of the invention a highly sensitive (shot noise limited) measurement of the absorption of the sample is obtained using only low frequency, WM detection methods. The use of the autobalancing circuitry allows very sensitive measurements with these low modulation frequencies, thus allowing one to use inexpensive, stable, and standard electrical components. The photodetectors used can also be much larger than for RF modulation allowing much easier alignment and ruggedness of the optical system. In addition, modulation of the laser beam can be performed within the laser itself, eliminating the need for additional optical components such as optical phase or frequency modulators, further simplifying the system.

The implementation of a grating tuned laser, wavelength modulation with phase sensitive detection, and the noise cancellation circuit provide many advantages over conventional systems, including: (a) easy, simple, controllable, laser tuning, allowing the diode laser to be scanned while maintaining constant laser power, (b) signal output that is substantially independent of temperature, (c) zero baseline signal measurement, (d) flexibility of detection frequency, allowing choice of an optimal detection frequency to minimize spurious signals, (e) the ability to make the absorption measurement at a single frequency, e.g. the absorption maximum, rather than scanning the laser frequency over the entire absorption line as is necessary in conventional non-zero baseline methods, and (f) elimination of laser power and system path variations in absorption signal by normalizing the final signal by the DC power received from the signal beam.

BRIEF DESCRIPTION OF THE FIGURES

These and other features, aspects and advantages of the present invention will become better understood with regard to the following descriptions, appended claims and accompanying drawings in which:

DETAILED DESCRIPTION

Figure 1:
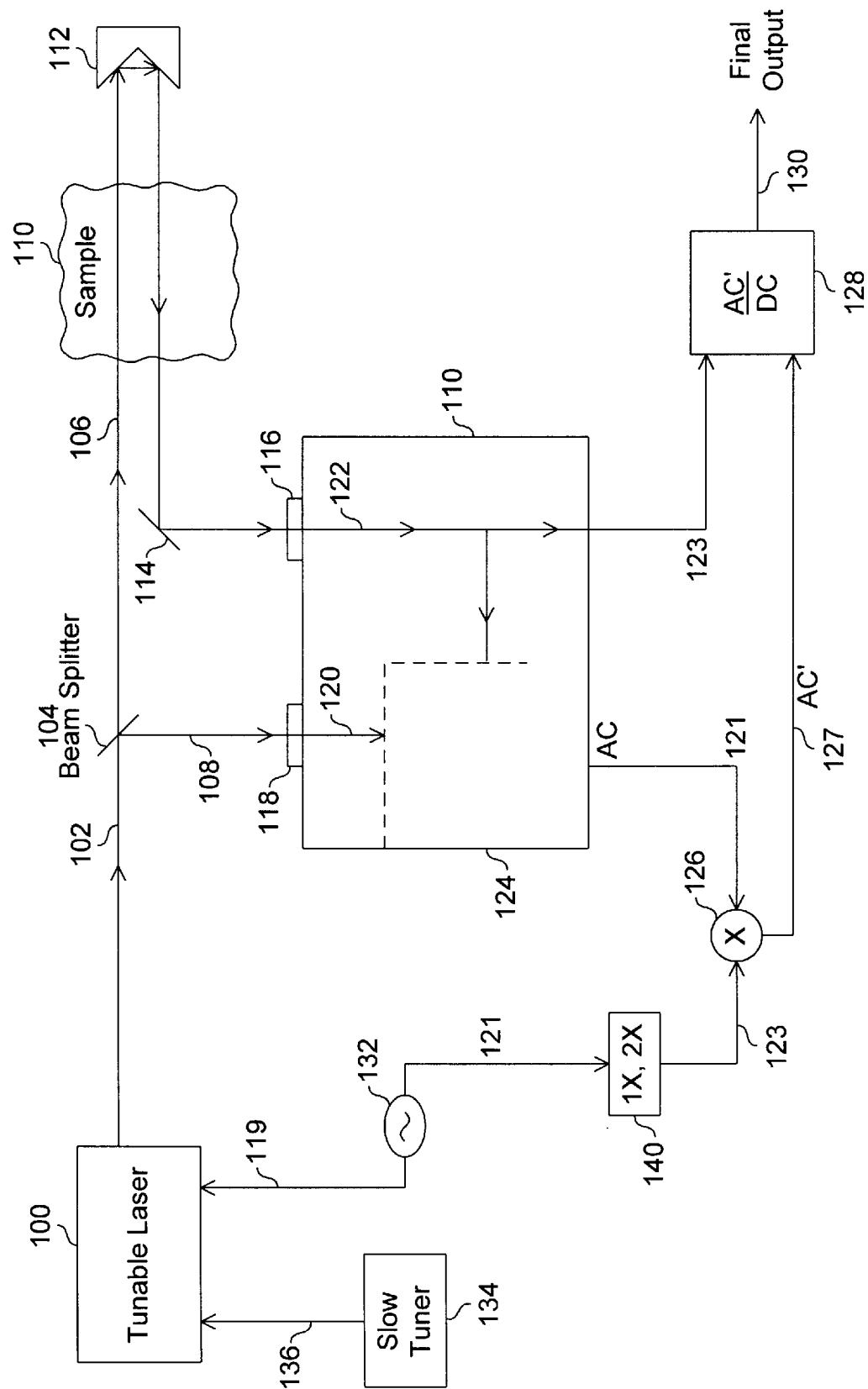
FIG. 1 is a block-schematic diagram of a laser absorption sensor system according to an embodiment of the invention.

Referring to FIG. 1, a tunable external cavity diode laser 100 generates a laser beam following optical path 102. The laser beam is wavelength modulated by periodically tuning laser 100 at a rate between one and one hundred KHz or higher, the modulation frequency. Laser 100 is tuned over a frequency range typically small in comparison to an absorption line width to be probed, but large in comparison to the line width of the laser; however, larger or smaller frequency ranges could be used.

A modulation signal generated at a modulation frequency by signal source 132 is transmitted by first signal source lead 119 to laser 100. The signal is used to drive the modulation of the laser beam frequency. A frequency shift is induced in the laser beam by the modulation signal, where the frequency shift is substantially proportional to the modulation signal amplitude. The frequency shift can be induced through a tuning mechanism such as a grating which is physically vibrated by the modulation signal at the modulation frequency, or through other conventional methods.

Referring to FIG. 1, a tunable laser 100 produces a wavelength modulated laser beam on an output beam path 102. The laser beam on path 102 is directed to a beam splitter 104. Beam splitter 104 splits the laser beam on path 102 into two beams, a signal beam on beam path 106 and a reference beam on beam path 108. The signal beam passes through beam splitter 104 and continues through sample container 110, where optical absorption characteristic of the sample contained in sample container 110 takes place. The signal beam is then reflected by mirror 112 back through sample container 110 and onto mirror 114. Mirror 114 directs the signal beam onto signal photodetector 116.

Reference beam reflected from beam splitter 104 onto beam path 108 is incident on photodetector 118. Photodetectors 116 and 118 provide output photo-currents at output leads 120 and 122, respectively. The output photo-currents from photodetectors 116 and 118 are proportional to the intensity of incident light on the respective photo sensitive surface of photodetectors 116 and 118. Thus the output photo-current at leads 120 and 122 are derived from the detection of the intensity of the reference and signal beams respectively and will be referred to as the reference and signal photo-currents.

Autobalancing circuit 124 inputs the signal and reference photo-currents on leads 120 and 122 respectively. Autobalancing circuit 124 produces an autobalanced signal on lead 121 which retains the absorption signal contained in the signal photo-current at the modulation frequency but has a significantly reduced noise level. The autobalanced signal on lead 121 is applied to a phase sensitive, lock-in amplifier 126.

A demodulation frequency signal on lead 123 is supplied to the phase sensitive lock-in amplifier 126. The demodulation frequency signal originates at signal source 132. Signal source 132 outputs the modulation frequency signal, the same signal used to tune the tunable laser 100, on lead 121 to frequency doubler 140. Frequency doubler 140 can be set to either pass the modulation frequency signal unaltered on lead 123 to phase sensitive lock-in amplifier 126, or to double the frequency of the modulation frequency signal and output the resulting modified modulation frequency signal on lead 123 to phase sensitive lock-in amplifier 126. The signal modified or not on lead 123 is called the demodulation frequency signal.

Phase sensitive lock-in amplifier 126 demodulates the autobalanced signal at the demodulation frequency, extracting the absorption information contained in the autobalanced signal at the demodulation frequency. If the demodulation frequency is the same as the modulation frequency the demodulated signal will be proportional to the first derivative of the absorption cross section of the sample at the central modulated laser frequency, and if the demodulation frequency is twice the modulation frequency the demodulated signal will be proportional to the second derivative of the absorption cross section of the sample at the central laser frequency.

Phase sensitive lock-in amplifier 126 outputs the demodulated autobalanced signal on lead 127 to divider circuit 128. In addition, photodetector 116 provides the signal photo-current signal on output lead 122 to divider circuit 128 through input lead 123. Divider circuit 128 divides the demodulated autobalanced signal on lead 127 by the DC component of the signal photo-current from input lead 123. This insures that the final output signal from divider circuit 128 is independent of the total incident power illuminating the sample in sample container 110. The final output signal comprises the AC/DC output signal on lead 130.

In a first embodiment, phase sensitive lock in amplifier 126 demodulates the autobalanced signal on lead 121 at the demodulation frequency provided on lead 123, where the demodulation frequency is the same frequency as the modulation frequency used to modulate the tunable laser 100. In this case, the demodulated final output signal at output lead 130 is proportional to the derivative of the absorption cross section of sample 110 at the central modulated laser frequency. This is because the frequency modulation of the laser beam is transformed into an amplitude modulation by the absorbing species in sample 110, and the magnitude of the amplitude modulation is proportional to the slope of the absorption cross-section.

Figure 2A:
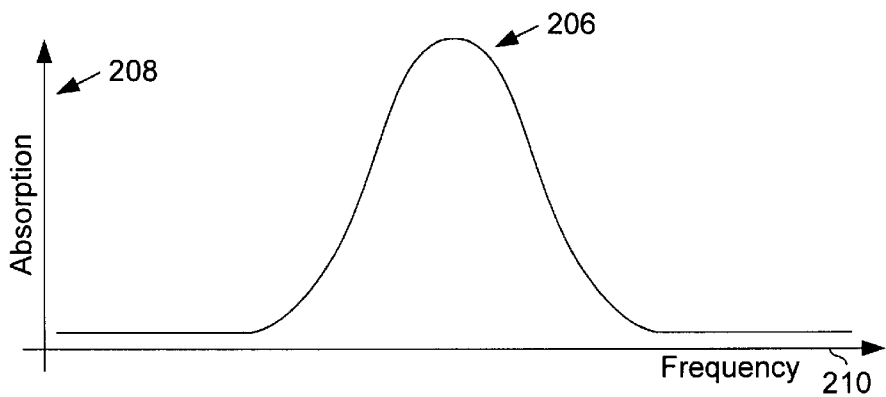
FIG. 2A is a graph showing the absorption cross section for a transition in a typical atomic or molecular species as a function of frequency.

FIGS. 2A, 2B, 2C and 2D illustrate the transformation of a frequency modulated laser beam into an intensity modulated beam as it passes through an absorbing sample. FIG. 2A is a graph of the absorption curve 206 for a transition in a typical atomic or molecular species as a function of frequency. Vertical axis 208 has units of absorption and horizontal axis 210 has units of frequency.

Figure 2B:
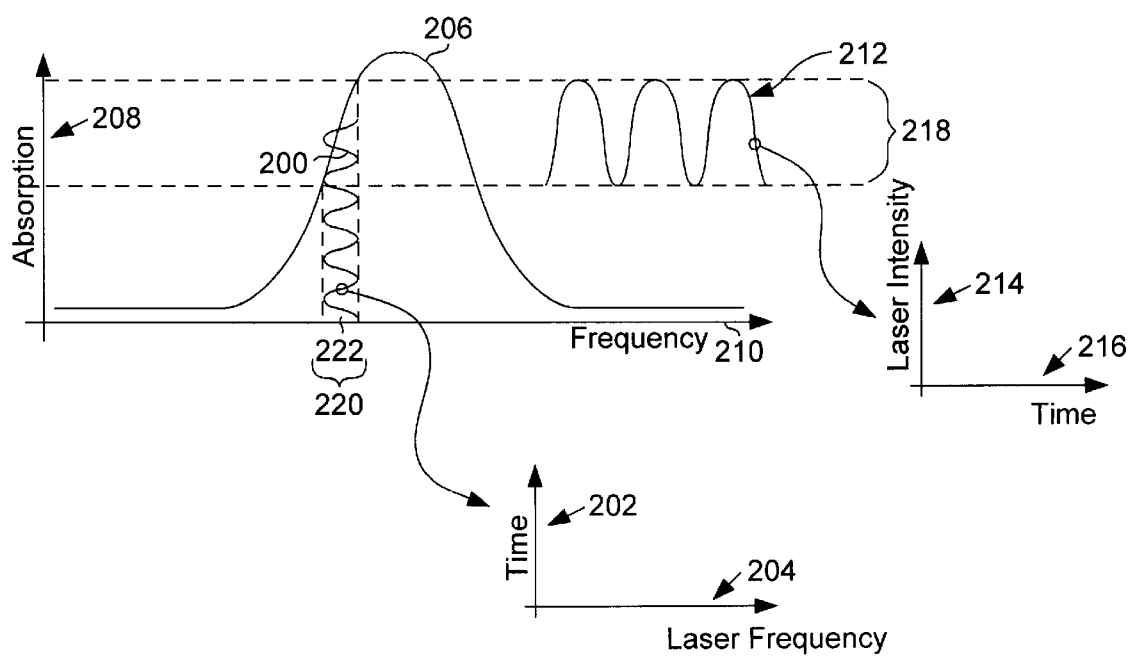
FIG. 2B is a graph showing the effect that the absorption cross section for a transition in a typical atomic or molecular species has on the frequency modulated laser beam.

Referring to FIG. 2B, a frequency modulated beam is represented by laser frequency graph 200, showing time on vertical axis 202 and laser frequency on horizontal axis 204. The absorption curve 206 illustrates absorption on vertical axis 208 of a sample species as a function of laser frequency on horizontal axis 210. As the modulated laser frequency oscillates the absorption of the laser by the sample varies, resulting in an intensity modulated output laser beam. Output laser intensity is shown on graph 212 with laser intensity on vertical axis 214 and time on horizontal axis 216. It follows that the amplitude variations 218 in the output laser intensity shown in curve 206 will be proportional to the difference in absorption over the range of frequencies 220 scanned by the modulated laser beam. The amplitude variations 218 are thus substantially proportional to the slope of absorption curve 206 at the central modulated laser frequency 222.

Figure 2C:
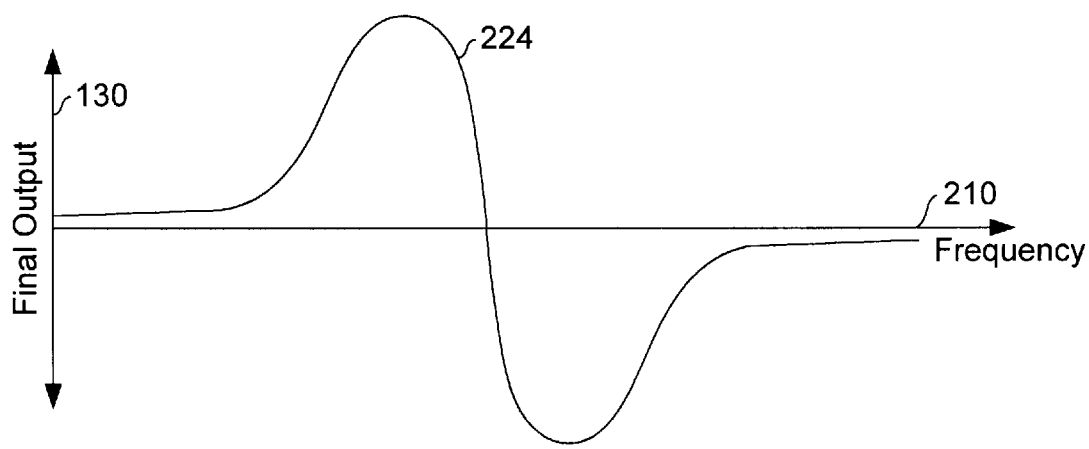
FIG. 2C is an example of the demodulated output signal of the absorption system of the present invention when demodulated at the modulation frequency.
Figure 2D:
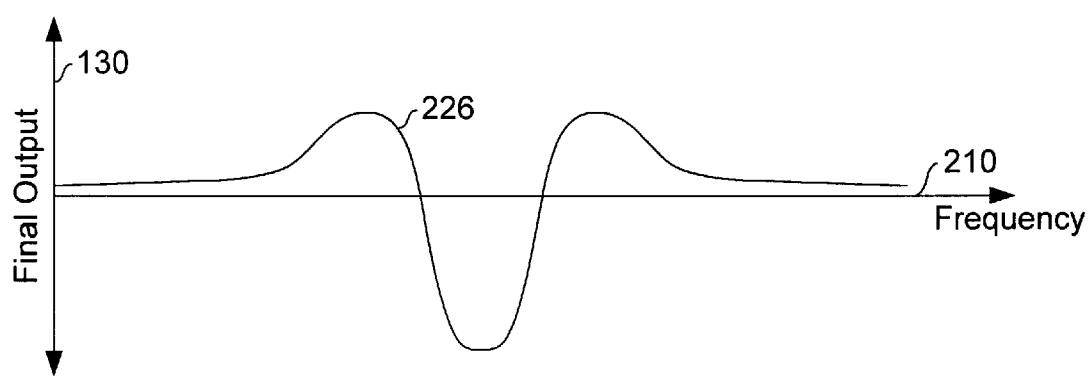
FIG. 2D is an example of the demodulated output signal of the absorption system of the present invention when demodulated at twice the modulation frequency.

Referring again to FIG. 1, slow tuner 134 provides an output signal over lead 136 to tunable laser 100. Slow tuner 134 is used to slowly scan the laser frequency over the entire range at which the sample species absorbs. The final output signal on lead 130 then traces out the derivative 224 of absorption curve 206 of the absorbing sample, as shown in FIG. 2C. The total number of absorbing species in sample 110 under investigation can be derived from derivative 224 of absorption curve 206 in a conventional manner.

In a second embodiment, the central modulated laser frequency is tuned to the frequency of maximum absorption by a specific species of interest in sample 110. Phase sensitive lock in amplifier 126 demodulates the autobalanced signal on lead 121 at the demodulation frequency provided on lead 123. In this embodiment, the demodulation frequency is twice the modulation frequency used to modulate the tunable laser 100. As is well known in the art, when the demodulation frequency is twice the modulation frequency the demodulated final output signal will be proportional to the second derivative 226 of the absorption curve 206 of the sample at the central modulated laser frequency, shown in FIG. 2D. The second derivative 226 of absorption curve 206 of the sample will be maximum at the frequency of maximum absorption, and will furthermore be substantially proportional to the concentration of the species of interest in sample container 110.

Figure 3A:
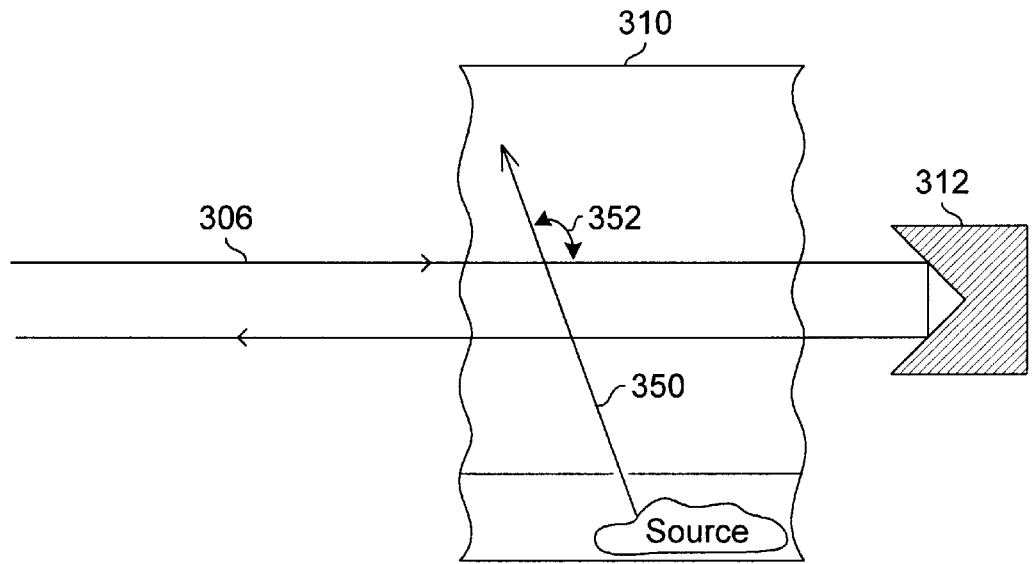
FIG. 3A is a block-schematic diagram of an embodiment of the invention for determining the velocity of a species within a molecular beam.

In a third embodiment, shown in FIG. 3A, signal laser beam 306 is incident on a molecular beam 350 propagating at a specific angle 352 relative to signal laser beam 306. Signal laser beam 306 is passed through sample molecular beam 350, reflected by mirror 312 and passed back through molecular beam 350. The propagation direction of laser beam 306 on the second pass through molecular beam 350 is anti-parallel to the propagation direction of sample laser beam 306 on the first pass.

The third embodiment is otherwise equivalent to the first embodiment of FIG. 1. However, when the laser frequency is scanned over the region which the sample species absorbs by a signal on lead 136 from slow tuner 134, two absorption signals will be observed. The absorption from the first pass through the sample is frequency shifted relative to the absorption from the second pass. The frequency shift is due to the Doppler Effect, whereby a frequency shift in the absorption frequency of absorbing molecules is substantially proportional to the velocity of the absorbing molecules in the propagation direction of the laser beam. By measuring the frequency shift between absorption signals from the first and second passes, the mean velocity of the absorbing species in the molecular beam can be determined. If the species concentration is known, by using one of the above methods, or otherwise, the number of molecules of that species crossing a plane perpendicular to the laser beam per unit time can be determined. This quantity is referred to as "flux" and is important for many material processing applications.

Figure 3B:
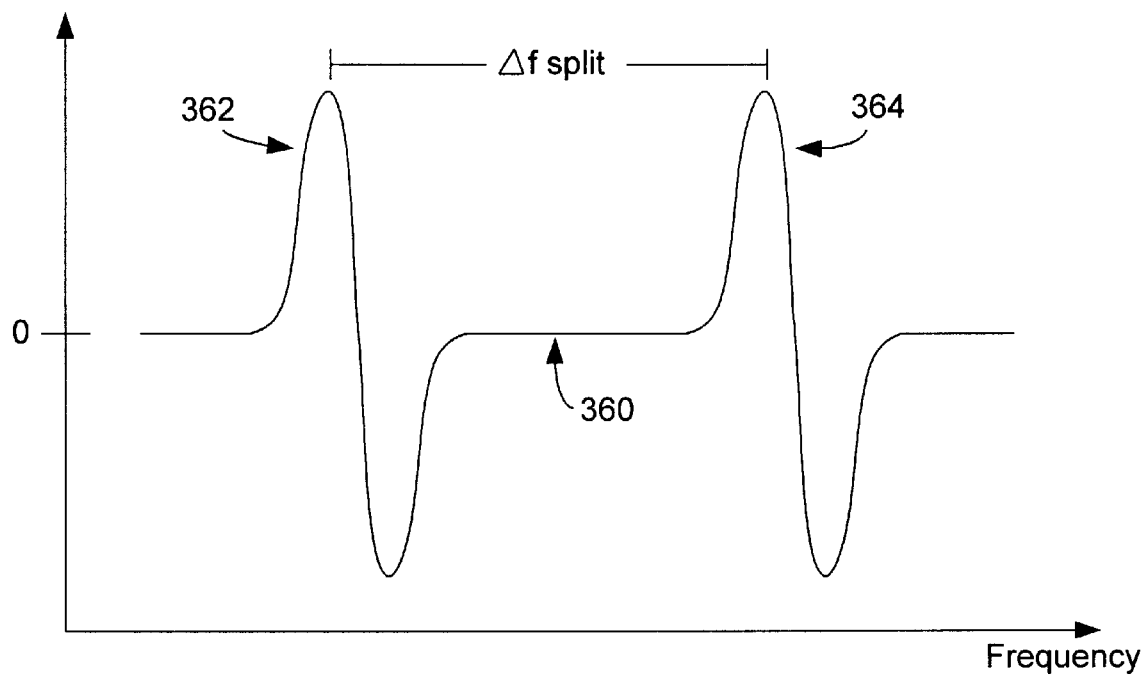
FIG. 3B is a plot showing Doppler shifted absorption signals.

FIG. 3B shows a plot of the derivative of the absorption curve 360 of an absorbing species in accordance with the third embodiment. The first absorption region 362 of curve 360 is from the first pass of the laser beam through the molecular beam and is clearly separated and frequency shifted relative to the second absorption region 364 of curve 360 from the second pass of the laser beam through the molecular beam.

Figure 4:
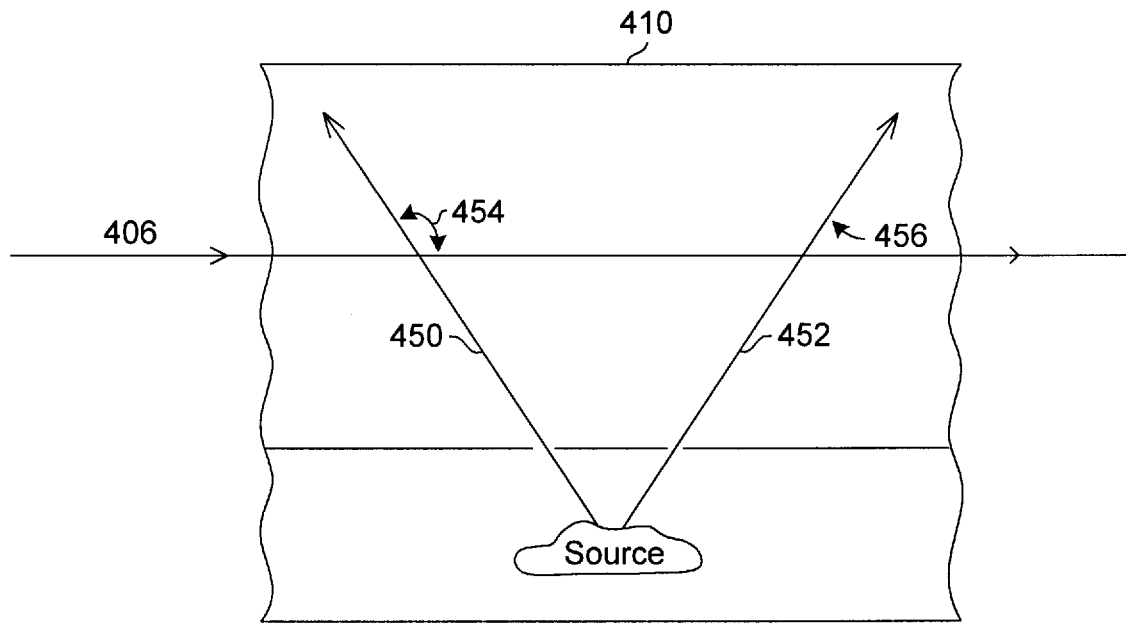
FIG. 4 is a block-schematic diagram of an embodiment of the invention for determining the relative velocity of a species between two molecular beams.

In a fourth embodiment, shown in FIG. 4, the signal laser beam 406 is incident on a pair of molecular beams 450 and 452. The propagation directions of molecular beams 450 and 452 are such that they form angles 454 and 456 with signal laser beam 406. In a similar manner to the third embodiment, the absorption cross section of the first molecular beam will be frequency shifted relative to the absorption cross section of the second molecular beam by the Doppler Effect. The frequency shift allows the relative velocity and flux of the two beams to be determined.

Figure 5A:
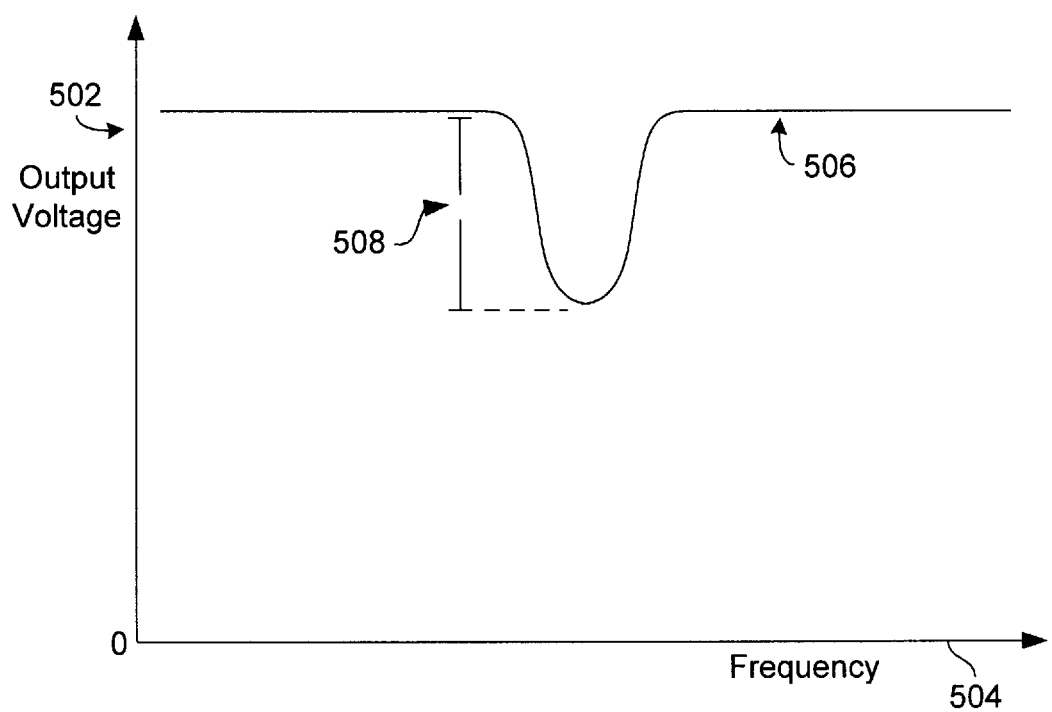
FIG. 5A is a graph of the output signal of a conventional laser absorption system as it is scanned over an absorption line.

FIG. 5A shows a sample output from a conventional system using direct detection, i.e. without modulation of the laser beam, and with an autobalancing circuit such as that of Hobbs. The output voltage from the autobalancing circuit is shown on the vertical axis 502 plotted against the laser frequency on the horizontal axis 504. Since photodetectors detect light intensity, when the absorption signal is zero, the output voltage is maximum. As the frequency of the laser is scanned over the absorption line, the output voltage will dip due to the absorption of the laser beam by the sample as shown by the absorption signal curve 506. In order to accurately measure the peak height 508 of the absorption signal of the sample, both the baseline voltage, i.e. the zero absorption output voltage, and the output voltage due to the sample absorption must be measured.

Figure 5B:
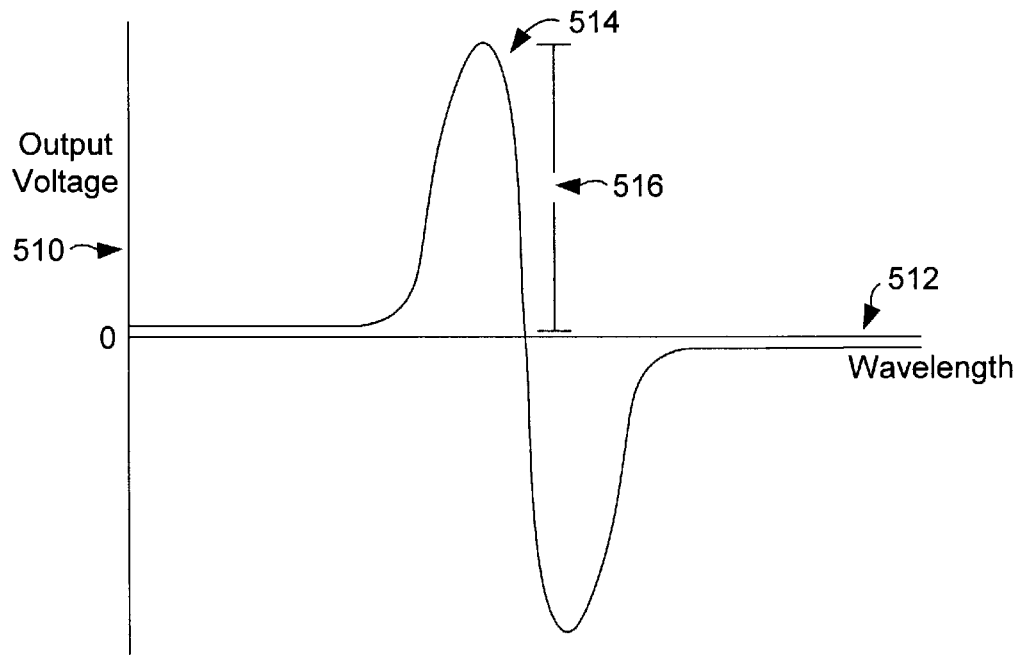
FIG. 5B is a graph of the output signal of an embodiment of the present invention as it is scanned over an absorption line.

In contrast, the present invention allows for a zero baseline measurement. FIG. 5B shows a sample output from the first embodiment of the invention. The final output voltage from output lead 130 of FIG. 1 is shown on the vertical axis 510 as a function of central laser frequency on the horizontal axis 512. The absorption curve 514 traced out in FIG. 5B is the derivative of the absorption cross section of the absorbing species, as explained previously. Since the slope of the absorption cross section is generally zero when the absorption is zero, the output voltage for laser frequencies which give zero absorption will also be zero. As the central laser frequency is scanned over the absorbing frequency region, the absorption signal measured will be absolute, i.e. need not be adjusted for a baseline signal. The absorption signal can thus be extracted by making an absolute measurement of peak height 516 of absorption curve 514.

Figure 6A:
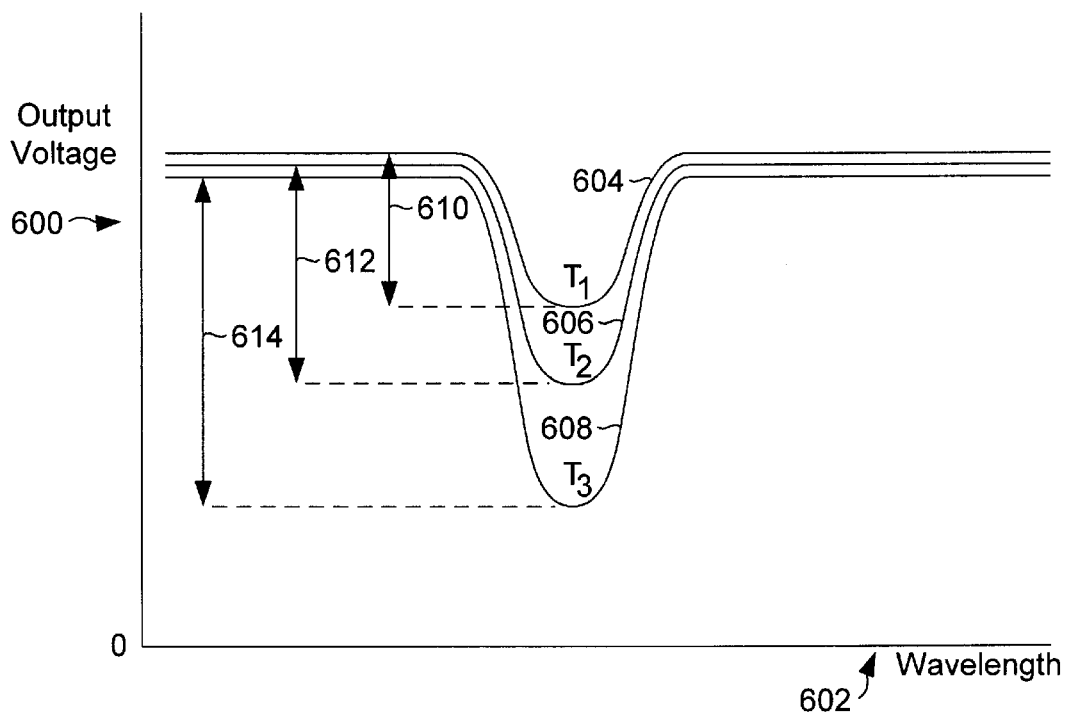
FIG. 6A is a graph showing the temperature dependence of the output signal of a conventional laser absorption system as it is scanned over an absorption line.

FIG. 6A shows the dependence of a sample output on the temperature of the detectors and signal processing circuitry in a conventional system using direct detection, i.e. without modulation of the laser beam, and with an autobalancing circuit such as that of Hobbs. The output voltage from the autobalancing circuit is shown on the vertical axis 600 plotted against the laser frequency on the horizontal axis 602. Absorption signal curves 604, 606 and 608 correspond to measurements made at temperatures $T_1$, $T_2$ and $T_3$ respectively, where $T_3$ is greater than $T_2$ which is greater than $T_1$. Peak absorptions 610, 612 and 614 corresponding respectively to absorption signal curves 604, 606, and 608, show the temperature dependence of the absorption signal. Peak absorptions for this system are substantially proportional to the temperature. For large temperature variations, for example zero to one hundred degrees Fahrenheit, the difference in peak absorptions can typically be as high as twenty percent. Temperature dependence of absorption measurements complicates determination of sample concentrations and other sample properties.

Figure 6B:
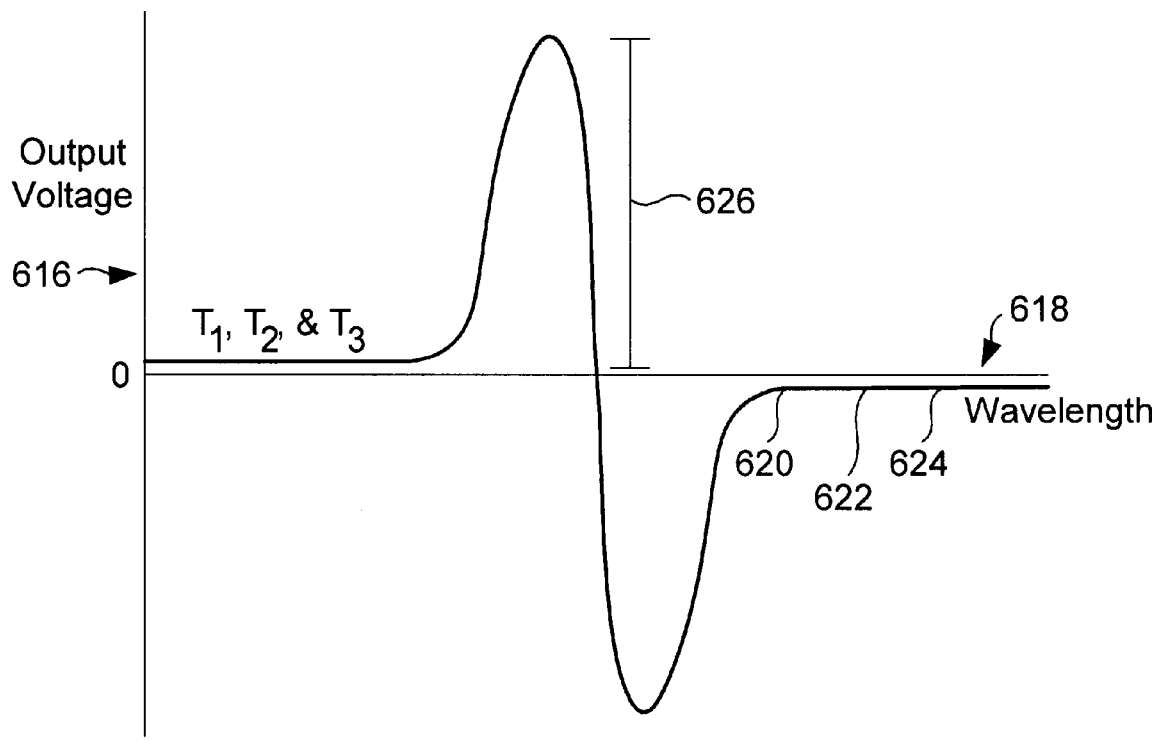
FIG. 6B is a graph showing the temperature independence of the output signal of an embodiment of the present invention as it is scanned over an absorption line.

In contrast, the present invention has substantially no dependence of the absorption measurements on the detector and signal processing circuitry. FIG. 6B shows a sample output from the first embodiment of the invention. The final output from output lead 130 of FIG. 1 is shown on the vertical axis 616. The final output is plotted as a function of central laser frequency on the horizontal axis 618 for three temperatures, $T_1$, $T_2$, and $T_3$. $T_3$ is greater than $T_2$ which is greater than $T_1$. The absorption curves 620, 622, and 624 correspond respectively to measurements made at temperatures $T_1$, $T_2$ and $T_3$. Curves 620, 622 and 624 are overlapping indicating the temperature independence of the output of the present invention. Thus the measurement of the peak height 626 can be used directly to determine the sample concentration, without the need for a temperature control system or temperature calibration of the instrument. The ability to make temperature independent measurements allows for a versatile laser absorption sensing system capable of functioning without calibration under a variety of environmental conditions.

In the laser absorption sensor system of the present invention, the tunable laser can be of any type, however, it must be capable of fast short range tuning to allow tuning at the modulation frequency (1–100 KHz). In addition, the laser should have long range tuning exceeding the range over which the species absorbs light, ideally approaching one gigahertz or more. It is also desirable to have a laser with a narrow line width to increase sensitivity. There are many suitable laser choices. One possible choice is an external cavity diode laser such as New Focus Model No. 6200. In addition to the above attributes, this laser is characterized by high stability, low maintenance and low cost. Such a laser is easily tuned by mechanical motion of a mirror. Other possible laser types include a semiconductor Distributed Bragg Reflector (DBR) or Distributed Feedback Laser (DFB). DBR lasers can be purchased from Spectra Diode Labs and DFB lasers are available from any number of vendors including AT&T.

The beam splitter 104 and optical mirrors 112 and 114 are standard optical components well known to one skilled in the art. The sample container 110 can be of any material so long as it is transparent to the frequency of laser light used to probe the sample, and provides sufficient laser beam path length through the sample to give a measurable signal.

Photodetectors 116 and 118 are typically an optical detector such as photo-diodes, which are commonly available and well known to one skilled in the art. Specifically a detector manufactured by New Focus No. 2007 may be used.

The autobalancing circuitry 124 is configured to substantially match the DC components of the photo-current signals and subtract the resulting balanced signals. The scaling of the DC component should be done in such a way as to scale all components of the signal proportionally so that any noise components common to both photo-currents will also match. In this manner an autobalanced photo-current is obtained with reduced noise. This can be accomplished by using the circuit of Hobbs (see U.S. Pat. No. 5,134,276).

The remaining electrical components, the slow tuner 134, signal source 132, frequency doubler 140, phase sensitive lock-in amplifier 126 and divider circuit 128 are all standard well known devices to one skilled in the art.

The previously described embodiments of the invention have many advantages including simple electronics. The low modulation frequency allows for simple electronics and data processing for this system. Low frequency inexpensive lock-in amplifiers may be used for phase sensitive detection, rather than complicated RF electronics. The simple electronics also allow for a very stable system with low drift. In addition, low modulation frequency allows the use of relatively large photo-diodes which greatly simplifies alignment of the optical system. The drawbacks of using a high frequency FM modulation scheme are thus avoided; however, the benefits of such a scheme are maintained. Specifically one still enjoys the use of a zero baseline modulation scheme that does not upshift the DC noise spectrum of the laser to the modulation frequency. This is accomplished using relatively simple and stable electrical and optical components so the system can be manufactured at low cost. An additional advantage is gained by implementing divider circuit 128. Dividing the demodulated absorption signal by the DC signal from the signal photodetector allows for a final output that is independent of incident laser power, and sample path-length, since the final output is then a relative absorption signal.

The foregoing description of a preferred embodiment of the invention has been presented for purposes of illustration and description. It is not intended to be exhaustive or to limit the invention to the precise forms disclosed. Many modifications and variations will be apparent to practitioners skilled in the art. It is intended that the scope of the invention be defined by the following claims and their equivalents.

What is claimed is:

1. A laser absorption system for measuring optical absorption of a sample across a range of wavelengths, and the laser absorption system comprising:

a tunable external cavity diode laser with a first input and a second input and an optical output, and the external cavity diode laser responsive to a sweep signal at the first input to mechanically sweep a beam at the output across the range of wavelengths, and the external cavity diode laser responsive to a modulation signal at the second input to dither the beam;

a signal source coupled to the second input of said tunable external cavity diode lasers and said signal source generating the modulation signal at a frequency suitable for derivative spectroscopy;

a splitter to split the laser beam into a reference beam and a signal beam and the signal beam intersecting the sample;

a reference photodetector that detects the reference beam and outputs a reference signal corresponding thereto;

a signal photodetector that detects the signal beam intersecting the sample and outputs an absorption signal corresponding thereto;

an autobalancer with a first input, a second input, and a first output, and the first input coupled to said reference photodetector to receive said reference signal, and the second input coupled to said signal photodetector to receive said absorption signal, and said autobalancer for processing the reference signal and the absorption signal and outputting at the first output a first autobalanced signal corresponding to the absorption signal with a reduction in a noise level thereof; and a demodulator with a first input, a second input and an output, and the first input coupled to said signal source, and the second input coupled to said first output of said autobalancer, and said demodulator for demodulating the first autobalanced signal with the modulation signal and generating at the output a derivative signal corresponding to a derivative of an absorption curve of the sample.

2. The laser absorption system of claim 1, wherein said autobalancer further includes; a second output and the autobalancer outputting at the second output a second autobalancing signal corresponding to the relative intensities of the reference beam and the signal beam intersecting the sample, and the laser absorption system further comprises:

a divider with a first input, a second input and an output, and the first input coupled to the second output of said autobalancer to receive said second autobalancing signal and the second input coupled to the output of said demodulator to receive the derivative signal and the divider outputting at the output an output signal corresponding to a division of the derivative signal by the second autobalancing signal.

3. The laser absorption system of claim 1, wherein said tunable external cavity diode laser further comprises:

a mechanically movable retroreflector responsive to the sweep signal at the first input to generate the beam sweeping across the range of wavelengths at the output.

4. The laser absorption system of claim 1, wherein said tunable external cavity diode laser further comprises:

a mechanically movable grating responsive to the modulation signal at the second input to dither the beam at the frequency suitable for derivative spectroscopy.

5. The laser absorption system of claim 1, further comprising:

a frequency doubler with an input and an output, and the input coupled to the signal source to receive the modulation signal and the output coupled to the first input of the demodulator, and the frequency doubler doubling a frequency of the modulation signal at the first input of said demodulator to such that the derivative signal corresponding to a second order derivative of the absorption curve of the sample.

* * * * *